United States Patent [19]

Stavinoha, Jr.

[11] Patent Number: 5,312,931
[45] Date of Patent: May 17, 1994

[54] RECOVERY OF 3,4-EPOXY-1-BUTENE FROM 1,3,-BUTADIENE OXIDATION EFFLUENTS

[75] Inventor: Jerome L. Stavinoha, Jr., Longview, Tex.

[73] Assignee: Eastman Chemical Company, Kingsport, Tenn.

[21] Appl. No.: 130,926

[22] Filed: Oct. 4, 1993

[51] Int. Cl.[5] .................. C07D 301/10; C07D 301/32; C07D 303/04
[52] U.S. Cl. ..................................... 549/538; 549/534
[58] Field of Search ......................................... 549/538

[56] References Cited

U.S. PATENT DOCUMENTS

5,117,012  5/1992  Stavinoha, Jr. et al. ........... 549/538

*Primary Examiner*—Joseph E. Evans
*Attorney, Agent, or Firm*—J. Frederick Thomsen; William P. Heath, Jr.

[57] ABSTRACT

Disclosed are improved processes for the recovery of 3,4-epoxy-1-butene (EpB) from an epoxidation effluent comprising EpB, butadiene, oxygen and butane obtained by the selective epoxidation of butadiene with an oxygen-containing gas in the presence of a catalyst and an inert gas. EpB is separated from the effluent by means of an absorption process using liquid mixture of butadiene and butane as the absorbent material. The inclusion of butane in the epoxidation and recovery processes permits the use of lower pressures in the absorption of the EpB product.

12 Claims, 1 Drawing Sheet

Fig.

RECOVERY OF 3,4-EPOXY-1-BUTENE FROM 1,3,-BUTADIENE OXIDATION EFFLUENTS

This invention pertains to the recovery of 3,4-epoxy-1-butene from an oxidation effluent comprising 3,4-epoxy-1-butene, unreacted 1,3-butadiene, butane as an inert diluent, and oxygen produced by the selective oxidation of 1,3-butadiene. More specifically, one embodiment of the present invention pertains to a process wherein the aforesaid oxidation effluent is intimately contacted with a mixture of liquid butane and 1,3-butadiene in an absorption zone to obtain a solution of 3,4-epoxy-1-butene in butane and 1,3-butadiene. Another embodiment of the invention pertains to the utilization of the 3,4-epoxy-1-butene recovery process as a means for accurately regulating the amount of the butane diluent and 1,3-butadiene reactant in the gas fed to an oxidation zone wherein 1,3-butadiene is selectively oxidized to 3,4-epoxy-1-butene.

U.S. Pat. Nos. 4,897,498 and 4,950,773 disclose processes for the manufacture of 3,4-epoxy-1-butene (referred to herein as EpB) by the selective epoxidation of 1,3-butadiene (referred to herein as butadiene) wherein butadiene is contacted with an oxygen-containing gas in the presence of certain silver catalysts. To achieve high yields of EpB (based on the butadiene consumed), especially when operating on a commercial scale, it is necessary to maintain the conversion of the butadiene at relatively low levels, e.g., from about 2 to 30 mole percent based on the butadiene fed to the epoxidation zone. The epoxidation effluent thus contains significant amounts of butadiene which must be recovered and recycled to the epoxidation zone. Obtaining a high yield of EpB also requires the presence of an inert gas diluent in the gas feed to the epoxidation zone. An inert gas such as methane, nitrogen, helium, or the like, constituting from about 25 to 85 mole percent of the gas feed to the epoxidation zone, is usually employed.

EpB is a very reactive compound which can be used to manufacture a variety of chemicals. Due to its reactivity, the recovery of EpB from epoxidation effluents must be performed under mild conditions to avoid the conversion of EpB to other undesired compounds such as butenediols and oligomers. It is possible to recover EpB directly from the epoxidation effluent by compressing the gaseous effluent to pressures sufficiently high to liquefy the EpB. However, the compression of the effluent would require the use of a series of compressors and heat exchangers to remove the heat of compression and maintain the EpB at a temperature which would minimize by-product formation.

The recovery of gaseous products by absorption techniques wherein a gaseous stream is contacted with a liquid absorbent, also referred to as an extractant or solvent, is well known. For example, in ethylene oxide processes wherein ethylene is epoxidized to ethylene oxide, water is used to absorb the ethylene oxide contained in the gaseous epoxidation effluent. A significant amount of the ethylene oxide reacts with the water to produce ethylene glycol. Because the objective of EpB manufacturing processes is the recovery of as much EpB as possible and since EpB has very limited water solubility, water is not a practical absorbent for the recovery of EpB.

An absorbent suitable for use in the recovery of EpB must be inert with respect to both EpB and to oxidation in the epoxidation zone. Saturated hydrocarbons such as pentane, hexane, cyclohexane, heptane, and the like form azeotropes with EpB which makes separation of EpB from the solvent quite difficult. The use of aromatic hydrocarbons, such as benzene, toluene, or xylene, and their presence in the EpB production system causes a decrease in the activity of the silver epoxidation catalyst due to complexation with the silver. Additionally, the temperatures that must be employed with these solvents to recover all the butadiene in a pressure distillation column cause losses of EpB due to polymerization and reaction with active hydrogen compounds, e.g., water, butenediols, and/or higher EpB adducts.

U.S. Pat. No. 5,117,012 discloses a process for the recovery of EpB from an oxidation effluent comprising EpB, butadiene, an inert diluent gas, and oxygen by contacting the oxidation effluent with liquid butadiene in an absorption zone to obtain a solution of EpB in butadiene. The inert diluent gases specifically contemplated by the '012 patent are nitrogen and methane. Since the examples in the patent teach the use of about 37.7 weight percent (approximately 16.4 mole percent) butadiene in the reactor feed, the pressures required in the absorber for recovery of EpB would be about 10 bars or higher using reasonable temperatures, e.g., 5° to 20° C. Such high pressures result in a number of disadvantages such as the capital and operating costs for the compressor(s) required to achieve the high pressures, EpB losses through hydrolysis and oligomer formation caused by the temperatures produced by the compression of the reactor gas effluent, and butadiene losses due to polymerization resulting in lower overall yields and downtime.

I have found that EpB can be recovered from a substantially-gaseous, epoxidation effluent comprising EpB, butane, butadiene, and oxygen by intimately contacting the effluent with a mixture of liquid butane and butadiene in an absorption zone. I also have found that by the use of certain conditions within the absorption zone, a vapor effluent containing a predetermined concentration of butane and butadiene may be removed from the absorption zone and utilized as the diluent and reactant, respectively, to the epoxidation zone. One embodiment of our invention therefore pertains to a process for the recovery of EpB from a substantially-gaseous effluent from an epoxidation zone wherein butadiene is contacted with an oxygen-containing gas using butane as the inert diluent in the presence of a catalyst, to produce an epoxidation effluent comprising EpB, butane, butadiene, and oxygen which comprises feeding the effluent to an absorption vessel wherein the effluent is intimately contacted with a mixture of liquid butane and butadiene at a pressure of about 2 to 10 bars and a temperature of about 0° to 60° C. to obtain:

(1) a vapor effluent comprising butane, butadiene and oxygen from the upper section of the absorption vessel; and (2) a liquid effluent comprising EpB and butane and butadiene from the lower section of the absorption vessel;

wherein the butane:butadiene mole ratio of the liquid mixture with which the effluent is contacted is about 20:1 to 1:2. As used herein, the term butane refers to C-4 hydrocarbons in general such as normal butane, isobutane, cyclobutane and mixtures thereof. The butane used in the operation of the EpB production system described herein is comprised of approximately 95% normal butane with minor amounts of other C-4 and C-5 compounds.

The use of a mixture of butane and butadiene as the absorbent is economically advantageous as compared to the use of other organic materials which are extraneous to the EpB production system. For example, the use of another absorbent would increase costs due to the additional equipment required for its recovery in addition to the added cost of the absorbent material itself. Since butane can function as both the reactor diluent and an absorbent component the number of components in the process are minimized. Additionally, the use of a mixture of butane and butadiene reduces compression and utility costs since a much lower pressure is required for recovery of the EpB. Using a mixture of butane and butadiene also reduces the amount of butadiene needed in the EpB production system, thus reducing polymer formation and other related yield losses.

Figure 1:
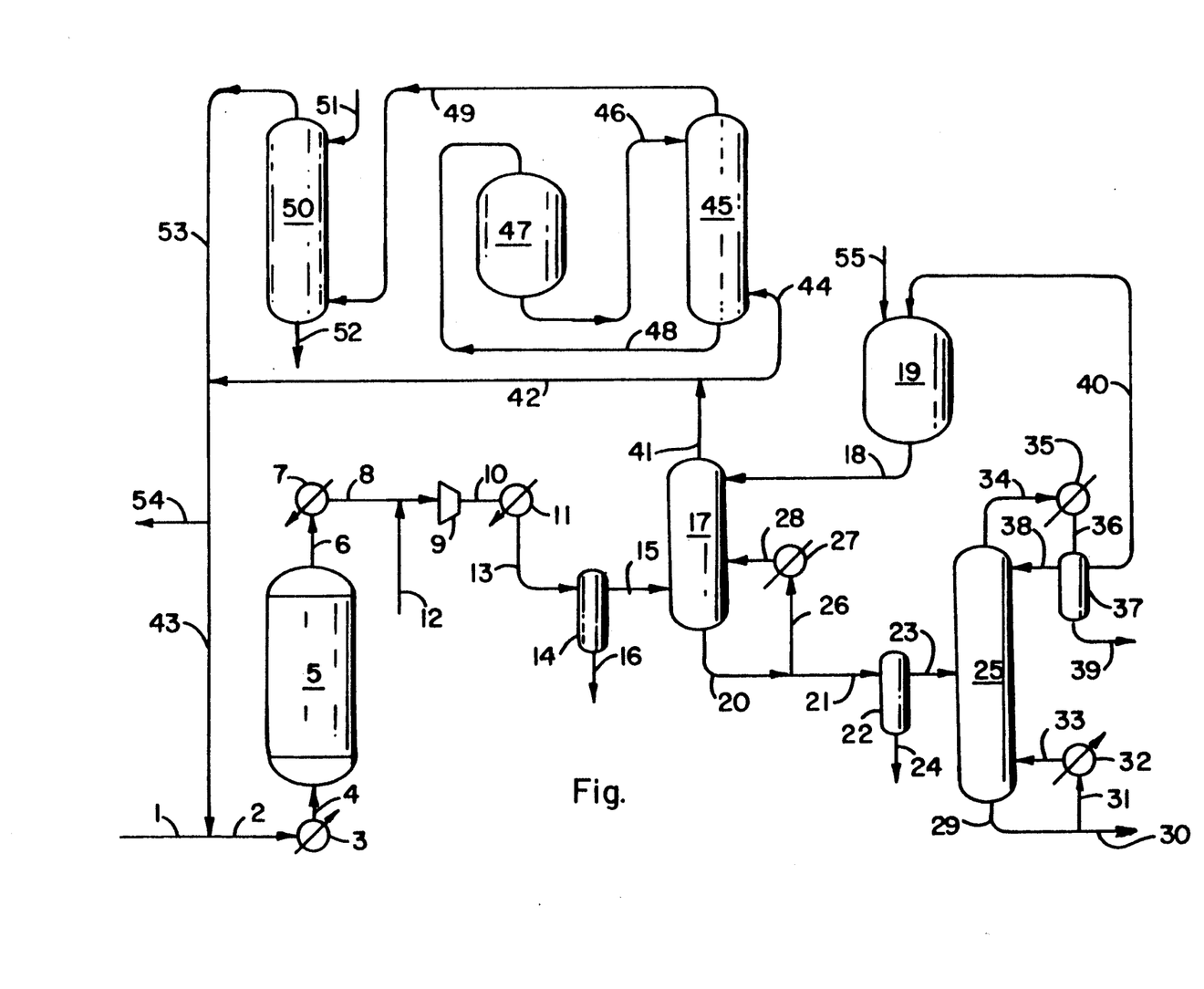
The accompanying FIGURE is a process flow diagram illustrating an EpB production system embodying the principles of the processes of the present invention. While the present invention is susceptible to embodiment in various forms, there is shown in the FIGURE and hereinafter described in detail preferred embodiments of the invention. However, the present disclosure is to be considered as an exemplification of the invention without limitation to the specific embodiments illustrated. The pressures referred to herein are given in bars absolute.

The present invention may be used in combination with any epoxidation process wherein butadiene is contacted with an oxygen-containing gas using butane as the diluent in the presence of a catalyst to produce an epoxidation effluent comprising EpB, butane, butadiene, and oxygen. The silver-catalyzed, epoxidation processes described in U.S. Pat. Nos. 4,897,498 and 4,950,773 are typical of those which may be employed in the epoxidation zone. The epoxidation zone comprises one or more reactors of any design that allows removal of the heat of reaction in order to prevent an exothermic temperature excursion from occurring. For example, a shell-and-tube design, typically used for ethylene oxide production, may be employed. Other types of reactor designs include multi-staged adiabatic reactors, fluidized bed reactors, moving or transport bed reactors and the like.

The feed to the epoxidation zone comprises butadiene, an oxygen-containing gas and butane which acts as an inert diluent gas. Generally, any oxygen ($O_2$) concentration up to the explosive limit can be used. In the present invention wherein butane functions as the inert diluent gas, relatively high oxygen concentrations, e.g., up to about 30 mole percent may be employed. The butadiene concentration typically is about 4 to 50 mole percent. The butadiene:oxygen mole ratio in the feed normally is maintained within the range of about 1:5 to 10:1. The inert gas, i.e., butane, usually constitutes about 25 to 85 mole percent of the total feed to the epoxidation zone. Normally, the feed also include a small amount, e.g., 1 to 40 parts per million (ppm) of a halide source such as 1,2-dichloroethane. Various other organic halides may be used, many of which are described in U.S. Pat. No. 4,950,773. The concentration of the organic halide in the feed more commonly is in the range of 2 to 10 ppm. The feed also may contain minor amounts, e.g., 6 mole percent or greater, of impurities such as up to about 4 mole percent water and up to 2 mole percent carbon dioxide. Some argon may also be present in the feed. The amount of argon is controlled by purging a small amount of the recycle gas. Typically, the amount of argon is maintained at less than 10 percent.

Although the reactor of the epoxidation zone may be operated at pressures ranging from 0.1 to 20 bars, pressures in the range of about 1 to 3 bars normally are used. The epoxidation feed typically is heated to about 175° to 225° C. in a pre-heater prior to entering the epoxidation reactor. The temperature of the epoxidation effluent is maintained at about 190° to 250° C., preferably about 210° to 230° C., by adjusting the pre-heater temperature and/or the concentration of oxygen and/or the organic halide in the feed.

The silver catalysts described in U.S. Pat. No. 4,897,498 are examples of the epoxidation catalysts which may be used to convert butadiene to EpB. The catalyst preferably is a supported, cesium-promoted, silver catalyst.

The gaseous epoxidation effluent typically comprises about 0.5 to 6 mole percent EpB, about 4 to 50 mole percent butadiene, about 4 to 25 mole percent oxygen and about 25 to 85 mole percent inert (butane) gas. The effluent also contains a total of about 0.5 to 10 mole percent of water, carbon dioxide, acrolein, furan, vinylacetaldehyde, and crotonaldehyde, formed in the epoxidation zone. Unconsumed organic halide also is present in the epoxidation effluent. Typically the overall selectivity to EpB is about 88–95%. As used herein, the percent conversion of butadiene is:

$$\frac{\text{Moles butadiene converted}}{\text{Moles butadiene fed}} \times 100$$

and the percent selectivity to 3,4-epoxy-1-butene is:

$$\frac{\text{Moles butadiene converted to 3,4-epoxy-1-butene}}{\text{Moles butadiene converted}} \times 100$$

The epoxidation effluent is fed to a cooling/compression zone comprising one or more heat exchangers and one or more compressors wherein the effluent is pressurized to a pressure of about 3 to 10 bars absolute and cooled to a temperature of about 0° to 100° C. The cooling/compression zone may include a gas/liquid separator to remove any condensed liquids, e.g., water and/or butenediols (3-butene-1,2-diol and 2-butene-1,4-diol), from the pressurized and cooled effluent prior to feeding it to the absorption zone.

The absorption zone comprises a columnar, pressure vessel containing trays or a packing material which facilitates intimate gas/liquid contact. Examples of suitable packing material include Koch-Sulzer packing, Pall rings, Berl saddles, and Penn State packing. The absorption vessel normally is provided with means, such as a disengaging space above the packing, to prevent or minimize entrainment of liquids in the gas stream removed from the upper section thereof. The pressurized, cooled, substantially gaseous, epoxidation effluent is fed to the lower section of the absorption vessel, preferably near the bottom of the vessel. A mixture of liquid butane and butadiene is fed to the upper section, preferably near the top, of the absorption vessel and flows downward, thereby absorbing or scrubbing the EpB component from the upwardly-flowing epoxidation effluent. The butane:butadiene mole ratio of the absorber solvent normally is maintained in the range of about 20:1 to 1:2 with mole ratios of about 12:1 to 2:1 being preferred. A solution of EpB in butane and butadiene is removed from the base of the absorption vessel and a vapor comprising butadiene, butane, oxygen and carbon dioxide components of the epoxidation effluent is removed from the top of the vessel.

As stated hereinabove, the epoxidation effluent is intimately contacted with a mixture of liquid butane and butadiene in the absorption zone at a pressure of about 2 to 10 bars and a temperature of about 0° to 60° C. The absorption zone preferably is operated at pressures and temperatures of about 3 to 6 bars and about 10° to 50° C. to minimize the reaction of the EpB with the minor amounts of active hydrogen compounds present. In a preferred embodiment of my invention, the particular combination of pressure and temperature are selected to provide a predetermined concentration of butane and butadiene, e.g., about 30 to 95, preferably about 40 to 90, mole percent, in the vapor effluent removed from the absorption vessel. The ratio of butane to butadiene in the absorber solvent also determines the concentration of these components in the gas effluent from the absorber. Thus, the butane:butadiene mole ratio in the absorber solvent is maintained to provide an absorber gas effluent containing about 4 to 50, preferably about 7 to 20, mole percent of butadiene, and about 25 to 85, preferably about 40 to 80, mole percent of butane. The mole percent composition of the vapor effluent from the absorber may be determined by applying both Dalton's law and Raoult's law to the components of the absorber. The butane/butadiene-containing vapor effluent thus obtained can be recycled, directly or indirectly, to the epoxidation zone and provide all of the butadiene reactant and butane diluent for the epoxidation reaction.

The amount of the liquid butane and butadiene mixture fed to the absorption vessel can vary substantially depending, for example, on the particular vessel, packing material and conditions employed and the feed rate and composition of the epoxidation effluent fed. Generally, the weight ratio of the absorber solvent feed to epoxidation effluent feed is in the range of about 0.1:1 to about 0.6:1. The temperature of the liquid butane and butadiene fed typically is in the range of about 0° to 40° C.

A liquid effluent (absorption underflow) comprising a solution of EpB in butane and butadiene is removed from the base of the absorption vessel and is fed to a butane/butadiene recovery zone. A portion, e.g., up to about 95 volume percent, of the underflow may be recycled to the absorption vessel. The recycle stream optionally may be cooled by means of a heat exchanger and returned to the lower section of the absorption vessel to control or regulate the temperature therein. The concentration of EpB in the absorption underflow stream may vary substantially, e.g., from about 2 to 40 weight percent based on the total weight of the stream. Normally, the EpB concentration is in the range of about 5 to 15 weight percent (same basis). The underflow also contains minor amounts of water, diol and other materials, e.g., up to about 5 mole percent water and up to 2 mole percent diol. The mole ratio of the butane to butadiene in the underflow is about the same as the butane:butadiene mole ratio of the liquid absorption solvent fed to the absorber.

The butane/butadiene recovery zone comprises a distillation vessel, e.g., a column, a heat source at the base of the vessel, cooling means to condense vapor removed from the top of the vessel and a separator to separate water from the condensed liquid. The absorption column underflow may be fed to the mid-section of the recovery column to obtain (1) a gas effluent comprising a mixture of butane and butadiene from the upper section of the column and (2) a liquid effluent comprising crude EpB from the lower section of the column. The gas effluent contains a minor amount of water which may be removed from the EpB production system by condensing the effluent to obtain a two-phase, liquid mixture and separating the aqueous phase from the butane/butadiene phase. Water and butadiene or butane form a constant boiling mixture (azeotrope) having a boiling point of approximately 43° C. at 4.8 bars pressure. The water removal may be enhanced by recycling a portion, e.g., up to 95 weight percent, of the condensed butane/butadiene phase to the upper section of the butane/butadiene recovery vessel. The water-depleted butane/butadiene stream removed from the butane/butadiene recovery zone may be recycled, directly or indirectly, to the absorption zone along with fresh butane/butadiene. Fresh butadiene also must be added to make up for that consumed in the reactor zone. However, fresh butadiene may be added at any point in the recycle loop and it is not necessary that the makeup butadiene be added in the liquid mixture of butane and butadiene fed to the absorber.

A second embodiment of my invention concerns a process for the recovery of EpB from a substantially-gaseous, epoxidation effluent from an epoxidation zone wherein butadiene is contacted with an oxygen-containing gas using butane as the diluent in the presence of a catalyst to produce an epoxidation effluent comprising EpB, butane and butadiene which comprises the steps of:

(A) feeding the effluent to an absorption vessel wherein the effluent is intimately contacted with a mixture of liquid butane and butadiene at a pressure of about 2 to 10 bars and a temperature of about 0° to 60° C. to obtain:
  (1) a vapor effluent comprising butane, butadiene, and oxygen from the upper section of the absorption vessel; and
  (2) a liquid effluent comprising EpB, butane, and butadiene from the lower section of the absorption vessel;

(B) feeding the effluent of Step (A)(2) to a butane/butadiene recovery vessel operated at a pressure of about 2 to 6 bars and a temperature over the range of about 5° to 150° C. to obtain:
  (1) a gas effluent comprising a mixture of butane and butadiene from the upper section of the column; and
  (2) a liquid effluent comprising crude EpB from the lower section of the column;

(C) condensing the gas effluent of Step (B)(1) to obtain a two-phase mixture comprising water and butane/butadiene and separating water from the two-phase mixture to obtain a water-depleted butane/butadiene stream; and (D) recovering the water-depleted mixture of butane and butadiene.

The conditions employed within the butane/butadiene recovery column may vary significantly depending on the particular apparatus employed. The pressures and temperatures normally are within the range of about 2 to 6 bars and 5° to 150° C. The column preferably is operated at a column base pressure and temperature of about 2.5 to 5 bars and 100° to 130° C. and a column head pressure and temperature of about 2.5 to 5 bars and 5° to 50° C. To prevent the formation of butadiene polymerization products, the butane/butadiene recovery preferably is carried out in the presence of a polymerization inhibitor, such as a phenolic compound, e.g., tertiary butyl catechol or an aromatic amine oxide compound, e.g., Actrene 230 inhibitor supplied by Exxon. The polymerization inhibitor may be added to the upper section of the butane/butadiene recovery column. For example, we have found that the formation of low molecular weight, butadiene polymerization products is substantially suppressed by the addition of about 300 to 400 ppm Actrene 230 inhibitor, based on the amount of vapor removed from the column, to the top of the butane/butadiene recovery column by means of a low-flow addition device such as a syringe pump. The inhibitor also may be added to the base of the absorption vessel, e.g., with the liquid butane/butadiene feed, and transported to the butane/butadiene recovery zone in the liquid effluent stream obtained from the absorption vessel to reduce polymer formation in the transfer lines and tanks.

The liquid underflow obtained from the butane/butadiene recovery zone comprises EpB, typically 90 to 99 weight percent EpB, and minor amounts of butane, butadiene, vinyl acetaldehyde, butenediols, vinylcyclohexene, crotonaldehyde and higher boiling impurities. This crude EpB may be further purified by distillation wherein EpB is taken overhead and most of the impurities are removed from the base of the distillation column.

As described hereinabove, the absorption zone may be operated to provide a vapor effluent containing a predetermined amount of the inert diluent butane and reactant butadiene which can be fed to, and provide all of the butane diluent and the butadiene reactant for, the epoxidation zone. This advantageous method of supplying both the inert diluent and the butadiene reactant to the epoxidation zone constitutes another embodiment of the present invention. This embodiment concerns a process for the manufacture and separation of EpB which comprises the steps of:

I. feeding a gas comprising about 4 to 50 mole percent butadiene, about 5 to 30 mole percent oxygen and about 25 to 85 mole percent of butane as inert material to an epoxidation zone wherein butadiene is epoxidized to EpB;
II. removing from the epoxidation zone a gaseous epoxidation effluent comprising about 0.5 to 6 mole percent EpB, about 4 to 50 mole percent butadiene, about 4 to 25 mole percent oxygen and about 25 to 85 mole percent inert gas;
III. feeding the gaseous epoxidation effluent to a cooling/compression zone wherein the effluent is pressurized to a pressure of about 3 to 10 bars and cooled to a temperature of about 0° to 100° C.;
IV. feeding the effluent obtained from Step (III) to an absorption vessel wherein the effluent is intimately contacted with a mixture of liquid butane and butadiene at a pressure of about 2 to 10 bars and a temperature of about 0° to 60° C. to obtain:
  (1) a vapor effluent comprising about 25 to 85 mole percent butane as the inert diluent and about 4 to 50 mole percent butadiene from the upper section of the absorption vessel; and
  (2) a liquid effluent comprising EpB, butane, and butadiene from the lower section of the absorption vessel; and
V. feeding the effluent of Step IV (1) to the epoxidation zone;

wherein the butadiene fed in Step I and the inert diluent, i.e., butane, in Step I is provided by the effluent of Step IV (1). This 5-step embodiment may include an additional step wherein the effluent of Step IV (1) is fed to a carbon dioxide removal zone as described hereinafter.

Since the presence of significant amounts of carbon dioxide in the gas fed to the epoxidation zone detrimentally affects the activity of the epoxidation catalyst, the butane/butadiene-containing effluent gas optionally is passed through a carbon dioxide removal zone wherein the carbon dioxide concentration of the gas is reduced to less than about 2 mole percent, preferably less than about 1 mole percent and most preferably to less than about 0.5 mole percent. Carbon dioxide removal may be accomplished by various known means such as by absorption using alkali and alkaline earth hydroxides and carbonates such as sodium hydroxide, potassium hydroxide, sodium carbonate or potassium carbonate, amines such as monoethanolamine and diethanolamine and size exclusion techniques using membranes or molecular sieves.

The carbon dioxide removal zone may comprise, for example, an absorption vessel wherein the gas is intimately contacted with an aqueous solution of an alkali metal hydroxide such as potassium hydroxide and from which a carbon dioxide-depleted gas effluent is removed. Thus, the effluent gas is fed to the bottom section and the aqueous solution of the alkali metal hydroxide, e.g., a 30 to 50 weight percent aqueous solution of potassium hydroxide, is fed to the upper section of the carbon dioxide absorption vessel containing an appropriate packing material or trays. The pressure within the vessel typically is about 2 to 9 bars. If necessary, the carbon dioxide removal zone may include an alkali removal vessel (scrubber) wherein the carbon dioxide-depleted gas stream is contacted (scrubbed) with water to remove any alkali metal hydroxide or carbonate entrained in the gas removed from the carbon dioxide absorption vessel. Typical pressures and temperatures within the scrubber vessel are about 2 to 9 bars and 5° to 110° C.

Since oxygen is consumed in the epoxidation zone, the oxygen content of the butadiene-containing effluent gas obtained from the EpB absorption zone (or the carbon dioxide removal zone) is supplemented by an oxygen feed prior to feeding the gas to the epoxidation zone. Normally, an organic halide (discussed hereinabove) also is added to the effluent gas.

Referring to the accompanying FIGURE, a mixture comprising butane, butadiene, oxygen, and an organic halide is fed by conduit 2 to heat exchanger 3 wherein the mixture is preheated to a temperature of about 175° to 225° C. and then is fed via conduit 4 to epoxidation reactor 5. The epoxidation reactor may contain a plurality of steel tubes packed with a silver catalyst such as a cesium-promoted, supported, silver catalyst. The gas feed passes through the catalyst-containing steel tubes wherein butadiene is selectively oxidized to EpB and exits the epoxidation reactor through conduit 6. A heat exchange fluid is passed over the exterior of the reactor tubes to remove the heat of reaction. The temperature and pressure within conduit 6 typically is about 1 to 4 bars and 200° to 240° C.

The epoxidation effluent is fed to heat exchangers 7 and 11 and compressor 9 by conduits 6, 8 and 10 wherein the temperature of the effluent stream is reduced to about 0° to 100° C. and the pressure is increased to about 2 to 12 bars. Makeup butadiene may be added to conduit 8 via conduit 12. The cooled and pressurized effluent is transported by conduit 13 to gas/liquid separator 14 and then through conduit 15 to absorber 17. The function of gas/liquid separator 14 is the removal of materials such as butenediols and water which are liquefied by the cooling and compression of the epoxidation effluent stream.

A mixture of liquid butane and butadiene is fed from butane/butadiene recovery tank 19 through conduit 18 to the upper section of absorber 17 which contains a suitable packing material to provide intimate contact between the effluent fed by line 15 and liquid butane/butadiene mixture fed by line 18. The pressure and temperature within absorber 17 are within the ranges of about 2 to 10 bars and 0° to 60° C., provided that the combination of pressure and temperature maintains a liquid phase within the absorber. The conditions of pressure and temperature also are controlled to provide a predetermined concentration of both butane and butadiene in the gaseous effluent removed from the top of the absorber.

A liquid effluent comprising a solution of EpB in butane/butadiene is removed from the base of absorber 17 and transported via conduits 20 and 21 to water separator 22 and then through conduit 23 to the midsection of butane/butadiene recovery column 25. A portion, e.g., up to about 95 weight percent, of the liquid effluent stream may be recycled through conduits 26, heat exchanger 27 and conduit 28 to absorber 17. This recycle stream functions to provide additional cooling of the contents of the absorber.

The concentration of EpB in the liquid solution fed by line 23 to column 25 typically is about 5 to 25 weight percent based on the total weight of the solution. Column 25 typically is equipped with trays or a packing material and is operated at a base pressure and temperature of about 2.5 to 5 bars and 100° to 130° C. and a head (top) temperature of about 2.5 to 5 bars and 5° to 50° C. to vaporize substantially all of the butane/butadiene fed. A liquid stream of crude EpB is removed from column 25 and from the EpB production system via conduits 29 and 30. This stream may be further refined by one or more distillations to increase the purity of the EpB, e.g., up to 99+%.

The heat required to vaporize butane and butadiene in column 25 is provided by recycling a portion, e.g., up to 95 weight percent, of the liquid stream to column 25 by means of conduit 31, heat exchanger (reboiler) 32 and conduit 33. A vapor comprised of butane, butadiene, and a minor amount of water is removed from column 25 through conduit 34, condensed in heat exchanger 35 and fed by conduit 36 to water separator 37. Water collects in the lower section of separator 37 and is removed from the production system by conduit 39. Separation of the butane and butadiene mixture and water from the other materials fed to column 25 is enhanced by recycling a portion, e.g., from about 50 to 95 weight percent, of the condensed butane/butadiene to the column via line 38. A butadiene polymerization inhibitor also may be added to column 25, for example, by means of line 38. The remainder of the condensed butane/butadiene is transported by conduit 40 to butane/butadiene recovery tank 19. A mixture of fresh butane/butadiene also is fed to tank 19 by line 55. This stream may contain butadiene to make up for the amount consumed in reactor 5 in addition to the butadiene and butane vented in the purge.

A vapor effluent comprising butadiene, butane, and oxygen is removed from absorber 17 via conduit 41. Normally, the butadiene content of the vapor effluent is within the range of about 4 to 50, preferably about 7 to 20 mole percent. Additionally, butane usually constitutes about 25 to 85 mole percent of the total feed to the epoxidation zone. The butane/butadiene-containing vapor effluent is conveyed to epoxidation reactor 5 by conduits 42, 43, 2 and 4 and preheater 3 and provides both the butadiene reactant and the inert gas, i.e. butane, for the epoxidation reaction. When using this mode of direct recycle to the epoxidation reactor, a portion of the stream of conduit 43 is purged from the production system through conduit 54 to prevent an excessive accumulation of carbon dioxide in the system. Oxygen is combined via conduit 1 with the effluent of line 43 to bring the concentration of oxygen in the reactor feed to about 5 to 30 mole percent.

Alternatively, all or part of the vapor effluent removed from EpB absorber 17 via line 41 is transported by conduit 44 to a carbon dioxide removal zone comprising carbon dioxide absorber 45, aqueous alkali metal hydroxide tank 47 and scrubber 50. The vapor effluent is fed by conduit 44 to the lower section of absorber 45 which contains an appropriate packing material. An aqueous solution of an alkali metal hydroxide is fed via conduit 46 to the upper section of absorber 45 from aqueous alkali metal hydroxide tank 47. Carbon dioxide is absorbed by the conversion of the alkali metal hydroxide to a carbonate. The aqueous solution of alkali metal hydroxide/carbonate is removed from absorber 45 and returned to tank 47 by line 48. Alternatively, a hot carbonate carbon dioxide removal system wellknown to those skilled in the art may be used. A carbon dioxide-depleted vapor is removed from the top of absorber 45 and conveyed by conduit 49 to the lower section of scrubber 50 wherein any alkali metal compound entrained in the carbon dioxide-depleted vapor is removed. Water is fed by means of conduit 51 to the upper section of scrubber 50 and removed from the bottom of the scrubber through line 52. An alkali-free vapor stream is removed from the top of the scrubber and transported via lines 53, 43, 2 and 4 and preheater 3 to the epoxidation reactor as described previously. A small purge via line 54 is required to remove argon which is an impurity present in the oxygen feed to the epoxidation zone.

The processes provided by the present invention are further illustrated by the following example using the EpB production system described in the FIGURE. The flow rates are given in parts by weight. The epoxidation reactor employed fixed beds of the cesium-promoted, supported silver catalyst described in U.S. Pat. No. 4,897,498.

A gas mixture comprising butane (inert gas), oxygen, butadiene, water and 4–5 ppm 1,2-dichloroethane in methane is heated to 180° C. in preheater 3 and fed by line 4 to epoxidation reactor 5 at a rate of 23,780 parts per hour at a pressure of 2 to 2.5 bars. Methane is utilized as a means of delivering the 1,2-dichloroethane to the EpB reaction system and normally is not present in a concentration greater than 0.7 weight percent at any point in the process. The epoxidation effluent gas comprising methane, oxygen, butane, butadiene, water, carbon dioxide, EpB and high boilers are removed from reactor 5 via line 6 at the rate of 23,791 parts per hour and transported through heat exchangers 7 and 11 and compressor 9 by lines 6, 8, 10 and 13 to gas/liquid separator 114. Butadiene is fed via conduit 12 at a rate of 321 parts per hour. Water and butenediols are removed from separator 14 through conduit 16 at rates of 3.3 and 0.3 parts per hour, respectively.

The epoxidation effluent gas is fed via conduit 15 to the side and near the bottom of EpB absorber 17 which consists of a 1.8 m section of stainless steel pipe having an inside diameter of approximately 10 cm. The absorber is packed with 14.1 liters of 6.35 mm Penn State packing except for a 0.5 m vacant space at the top. A mixture of liquid butane and butadiene (91.6/8.4 weight percent) is feed at a pressure of 6.5 bars and a temperature of 20° C. by conduit 18 to the side and near the top of absorber 17 at a rate of 5764 parts per hour. The pressure and temperature within the absorber are 4.9 bars and 40° C. A liquid comprising butane, butadiene, EpB, water, butenediols and high boilers is removed from absorber 17 and transported by conduit 20 and 21 to separator 22. Water and butenediols are removed from separator 22 by line 24 at rates of 25.6 and 4.6 parts per hour, respectively, and the stream is fed through conduit 23 to the mid-section of butane/butadiene recovery column 25 at a rate of 5826 parts per hour. A portion of the conduit 20 stream is removed by line 26, cooled in heat exchanger 27 and recycled via conduit 28 to the lower section of absorber 20 at a rate of 11710 parts per hour.

Column 25 is operated at a base pressure and temperature of 4.8 bar and 125° C. and a top pressure and temperature of 4.8 bar and 45° C. A liquid stream comprising EpB, butenediols, and high boilers is removed from the base of column 25 and from the production system via conduits 29 and 30 at a rate of 372 parts per hour. A portion of the liquid stream of line 29 is removed by line 31, passed through heat exchanger 32 and fed via line 33 to the lower section of column 25 to maintain the base temperature of 125° C. therein. The crude EpB product of line 30 may be distilled to obtain an overhead EpB product having a purity in excess of 99 percent.

A vapor effluent comprising methane, oxygen, carbon dioxide, butane, and butadiene is removed from absorber 20 through line 41 at a rate of 24,019 parts per hour and is fed by line 44 to the lower sidewall of carbon dioxide absorber 45. The vapor effluent may be returned directly to epoxidation reactor 5 via lines 41, 42, 43, 2 and 4 and preheater 3 although the carbon dioxide present in the vapor has been found to adversely affect the epoxidation reaction. The carbon dioxide absorber consists of a 1.8 m section of stainless steel pipe having an internal diameter of 7.6 cm. An aqueous solution containing approximately 20 weight percent potassium hydroxide/carbonate is fed via conduit 46 to the upper section of, and removed via conduit 48 from the bottom of, absorber 45 at a rate of 9640 parts per hour. A carbon dioxide-depleted vapor effluent is removed from absorber 45 and fed at a rate of 24,914 parts per hour by conduit 49 to the lower section of scrubber 50 wherein any entrained potassium hydroxide/carbonate is removed by water fed through line 51 and removed by line 52.

The vapor effluent from scrubber 50 is transported to reactor 5 by lines 53, 43, 2 and 4 and preheater 4 at a rate of 23,780 parts per hour. A portion of the line 43 stream is purged (line 54) from the production system at a rate of 359 parts per hour. A mixture of methane, 1,2-dichloroethane and oxygen is combined with the line 40 stream at a rate of 225 parts per hour.

In the above example, EpB is produced at a rate of 0.24 Kg per liter catalyst per hour at an average butadiene conversion of 16.9 mole percent and an overall EpB yield of 88.5 percent. This EpB production rate is achieved by operating the described EpB production system continuously for a period of time exceeding 300 hours.

The compositions of some of the streams of the preceding example are set forth in Table I wherein the values given are weight percentages based on the total weight of the stream composition. Diols refers to a mixture of 3-butene-1,2-diol and 2-butene-1,4-diol and high boilers include vinyl acetaldehyde, crotonaldehyde and high molecular weight compounds.

TABLE I

| Conduit Stream | $O_2$ | $CO_2$ | $C_4H_6$ | $C_4H_{10}$ | EpB | $H_2O$ | Diols | High Boilers |
|---|---|---|---|---|---|---|---|---|
| 2 | 12.6 | 0 | 8.0 | 78.0 | 0 | 0.7 | 0 | 0 |
| 6 | 11.8 | 0.4 | 6.6 | 78.0 | 1.6 | 0.9 | 0 | 0 |
| 13 | 12.7 | 0.4 | 7.9 | 76.9 | 1.5 | 0.9 | <0.1 | 0 |
| 16 | 0 | 0 | 0 | 0 | 0 | 90.5 | 8.5 | 1.0 |
| 18 | 0 | 0 | 8.4 | 91.6 | 0 | 0 | 0 | 0 |
| 20 | 0 | 0 | 7.8 | 85.3 | 6.3 | 0.5 | 0.1 | <0.1 |
| 24 | 0 | 0 | 0 | 0 | 0 | 84.0 | 15.1 | 0.9 |
| 30 | 0 | 0 | 0 | 0 | 99.2 | 0 | 0.7 | 0.1 |

As has been described hereinabove, one embodiment of our invention is the use of the EpB absorber as the source of the butane diluent and butadiene reactant fed to the epoxidation reactor. For this purpose, the mole percent butadiene in the vapor effluent from the EpB absorber normally is maintained between about 4 and 50, preferably between about 7 and 20, mole percent and the mole percent butane is normally maintained between about 25 to 85 mole percent, preferably between about 40 to 80 mole percent. A wide variety of combinations of butane:butadiene ratios, pressure, and temperature may be employed within the absorber to produce vapor effluents containing such concentrations of butane and of butadiene. The EpB absorber preferably is operated within the range of 10° to 50° C. and 3 to 6 bars since cooling the epoxidation effluent to less than 0° C. is costly due to the equipment required and the increased operating costs involved and pressurizing the effluent significantly above 8 bars can cause a decrease in the overall yield of EpB due to its conversion to other compounds in the cooling/compression zone.

Tables II, III, and IV show the pressures (in bars absolute) which are required when using temperatures of 0° C. to 60° C. to produce vapor effluents containing 50, 60, 70, 80, and 90 mole percent of three different butane/butadiene mixtures. The temperatures (Temp., °C.) reported in Tables II, III, and IV are the temperatures of the vapor effluent as it exits the absorber. The data reported in Table II were the result of varying pressure and temperature within absorber 17 when (i) feeding a mixture of butane and butadiene in a butane:butadiene mole ratio of 93:7 to the absorber and (ii) removing a gas effluent comprising a mixture of butane and butadiene in a butane:butadiene mole ratio of 92.3:7.7 from the absorber. The data reported in Table III were the result of varying pressure and temperature within absorber 17 when (i) feeding a mixture of butane and butadiene in a butane:butadiene mole ratio of 90:10 to the absorber and (ii) removing a gas effluent comprising a mixture of butane and butadiene in a butane:butadiene mole ratio of 89:11 from the absorber. The data reported in Table IV were the result of varying pressure and temperature within absorber 17 when (i) feeding a mixture of butane and butadiene in a butane:butadiene mole ratio of 80:20 to the absorber and (ii) removing a gas effluent comprising a mixture of butane and butadiene in a butane:butadiene mole ratio of 78.2:21.8 from the absorber. The C-4 Concentration recited in each Table designates the combined concentrations of butane and butadiene in the gas effluent.

TABLE II

| Temp. | Pressure Required to Maintain C-4 Concentrations of: | | | | |
|---|---|---|---|---|---|
| | 50% | 60% | 70% | 80% | 90% |
| 0 | 2.03 | 1.69 | 1.45 | 1.27 | 1.13 |
| 4 | 2.42 | 2.01 | 1.73 | 1.51 | 1.34 |
| 8 | 2.80 | 2.33 | 2.00 | 1.75 | 1.55 |
| 12 | 3.28 | 2.74 | 2.35 | 2.05 | 1.82 |
| 16 | 3.75 | 3.13 | 2.68 | 2.35 | 2.09 |
| 20 | 4.29 | 3.57 | 3.06 | 2.68 | 2.38 |
| 30 | 5.98 | 4.98 | 4.27 | 3.73 | 3.32 |
| 40 | 7.78 | 6.48 | 5.56 | 4.86 | 4.32 |
| 50 | 10.00 | 8.33 | 7.14 | 6.25 | 5.55 |
| 60 | 13.00 | 10.83 | 9.28 | 8.12 | 7.22 |

To illustrate the significance of the data presented in Table II, feeding a 93:7 mixture of liquid butane/butadiene to the absorber at 40° C. and 4.86 bars results in a gas effluent containing 80 mole percent butane and butadiene (73.8 percent and 6.2 percent, respectively).

TABLE III

| Temp. | Pressure Required to Maintain C-4 Concentrations of: | | | | |
|---|---|---|---|---|---|
| | 50% | 60% | 70% | 80% | 90% |
| 0 | 2.04 | 1.70 | 1.46 | 1.27 | 1.13 |
| 4 | 2.42 | 2.02 | 1.73 | 1.51 | 1.35 |
| 8 | 2.81 | 2.34 | 2.00 | 1.75 | 1.56 |
| 12 | 3.29 | 2.74 | 2.35 | 2.06 | 1.83 |
| 16 | 3.77 | 3.14 | 2.69 | 2.35 | 2.09 |
| 20 | 4.30 | 3.58 | 3.07 | 2.69 | 2.39 |
| 30 | 5.99 | 4.99 | 4.28 | 3.74 | 3.33 |
| 40 | 7.80 | 6.50 | 5.57 | 4.88 | 4.33 |
| 50 | 10.04 | 8.37 | 7.17 | 6.27 | 5.58 |
| 60 | 13.05 | 10.87 | 9.32 | 8.16 | 7.25 |

TABLE IV

| Temp. | Pressure Required to Maintain C-4 Concentrations of: | | | | |
|---|---|---|---|---|---|
| | 50% | 60% | 70% | 80% | 90% |
| 0 | 2.08 | 1.73 | 1.48 | 1.30 | 1.15 |
| 4 | 2.45 | 2.04 | 1.75 | 1.53 | 1.36 |
| 8 | 2.84 | 2.37 | 2.03 | 1.77 | 1.58 |
| 12 | 3.31 | 2.76 | 2.37 | 2.07 | 1.84 |
| 16 | 3.81 | 3.17 | 2.72 | 2.38 | 2.12 |
| 20 | 4.34 | 3.61 | 3.10 | 2.71 | 2.41 |
| 30 | 6.04 | 5.03 | 4.31 | 3.77 | 3.36 |
| 40 | 7.88 | 6.57 | 5.63 | 4.93 | 4.38 |
| 50 | 10.18 | 8.48 | 7.27 | 6.36 | 5.65 |
| 60 | 13.23 | 11.02 | 9.45 | 8.27 | 7.35 |

The invention has been described in detail with particular reference to preferred embodiments thereof, but it will be understood that variations and modifications may be effected within the spirit and scope of the invention.

I claim:

1. Process for the recovery of EpB from a substantially-gaseous, effluent from an epoxidation zone wherein butadiene is contacted with an oxygen-containing gas in the presence of a catalyst and butane to produce an epoxidation effluent comprising EpB, butadiene, oxygen and butane which comprises feeding the effluent to an absorption vessel wherein the effluent is intimately contacted with a mixture of butane and butadiene at a pressure of about 2 to 10 bars and a temperature of about 0° to 60° C. to obtain:

(1) a vapor effluent comprising butadiene, oxygen and butane from the upper section of the absorption vessel; and (2) a liquid effluent comprising EpB, butadiene, and butane from the lower section of the absorption vessel;

wherein EpB is 3,4-epoxy-1-butene and butadiene is 1,3-butadiene.

2. Process according to claim 1 wherein the epoxidation effluent comprises about 0.5 to 6 mole percent EpB, about 4 to 50 mole percent butadiene, about 4 to 25 mole percent oxygen and about 25 to 85 mole percent butane and the amount of liquid absorber solvent employed is about 0.1 to 0.6 parts by weight per part by weight epoxidation effluent.

3. Process for the recovery of EpB from a substantially-gaseous, effluent from an epoxidation zone wherein butadiene is contacted with an oxygen-containing gas in the presence of a silver catalyst and butane to produce an epoxidation effluent comprising about 0.5 to 6 mole percent EpB, about 4 to 50 mole percent butadiene, about 4 to 25 mole percent oxygen and about 25 to 85 mole percent butane which comprises feeding the effluent to an absorption vessel wherein the effluent is intimately contacted with a mixture of liquid butane and butadiene at a pressure of about 3 to 6 bars and a temperature of about 10° to 50° C. to obtain:

(1) a vapor effluent comprising butadiene, butane, and the oxygen from the upper section of the absorption vessel; and (2) a liquid effluent comprising EpB, butane, and butadiene from the lower section of the absorption vessel;

wherein EpB is 3,4-epoxy-1-butene and butadiene is 1,3-butadiene.

4. Process according to claim 3 wherein the vapor effluent (1) contains about 4 to 50 mole percent butadiene and 25 to 85 mole percent butane, and liquid effluent (2) contains about 5 to 40 weight percent EpB.

5. Process for the recovery of EpB from a substantially-gaseous, epoxidation effluent from an epoxidation zone wherein butadiene is contacted with an oxygen-containing gas in the presence of a catalyst and butane to produce an epoxidation effluent comprising EpB, butadiene, oxygen and butane which comprises the steps of:

(A) feeding the effluent to an absorption vessel wherein the effluent is intimately contacted with a mixture of liquid butane and butadiene at a pressure of about 3 to 6 bars and a temperature of about 10° to 50° C. to obtain:

(1) a vapor effluent comprising butane, oxygen and butadiene from the upper section of the absorption vessel; and (2) a liquid effluent comprising EpB, water, butane, and butadiene from the lower section of the absorption vessel;

(B) feeding the effluent of Step (A)(2) to a solvent recovery vessel operated at a pressure of about 2.5 to 5 bars and a temperature in the range of about 5° to 130° C. to obtain:

(1) a vapor effluent comprising butane, butadiene and water from the upper section of the column; and (2) a liquid effluent comprising crude EpB from the lower section of the column;

(C) condensing the vapor effluent of Step (B)(1) to obtain a two-phase mixture comprising water and mixture of butane and butadiene and separating water from the two-phase system to obtain a water-depleted mixture of butane and butadiene; and (D) recovering the water-depleted mixture of butane and butadiene;

wherein EpB is 3,4-epoxy-1-butene and butadiene is 1,3-butadiene.

6. Process according to claim 5 wherein the epoxidation effluent comprises about 0.5 to 6 mole percent EpB, about 4 to 50 mole percent butadiene, about 4 to 25 mole percent oxygen and about 25 to 85 mole percent butane, the amount of liquid butane and butadiene employed is about 0.1 to 0.6 parts by weight per part by weight epoxidation effluent and liquid effluent (A)(2) contains about 2 to 60 weight percent EpB.

7. Process for the recovery of EpB from a substantially-gaseous, epoxidation effluent from an epoxidation zone wherein butadiene is contacted with an oxygen-containing gas in the presence of a silver catalyst and butane to produce an epoxidation effluent comprising about 0.5 to 6 mole percent EpB, about 4 to 50 mole percent butadiene, about 4 to 25 mole percent oxygen and about 25 to 85 mole percent butane which comprises the steps of:

(A) feeding the effluent to an absorption vessel wherein the effluent is intimately contacted with a mixture of liquid butane and butadiene at a pressure of about 3 to 6 bars and a temperature of about 10° to 50° C. to obtain:

(1) a vapor effluent comprising butadiene, oxygen, and butane from the upper section of the absorption vessel; and (2) a liquid effluent comprising about 5 to 40 weight percent EpB and butadiene and butane from the lower section of the absorption vessel;

(B) feeding the effluent of Step (A)(2) to a solvent recovery column operated at a column base pressure and temperature of about 2.5 to 5 bars and about 100° to 130° C. and at a column head pressure and temperature of about 2.5 to 5 bars and about 5° to 50° C. to obtain:

(1) a vapor effluent comprising butadiene and butane from the upper section of the column; and (2) a liquid effluent comprising crude EpB from the lower section of the column;

(C) condensing the vapor effluent of Step (B)(1) to obtain a two-phase mixture comprising water and butadiene/butane and separating water from the two-phase mixture to obtain a water-depleted butadiene/butane stream; and (D) recovering the water-depleted mixture of butane and butadiene;

wherein EpB is 3,4-epoxy-1-butene and butadiene is 1,3-butadiene.

8. Process for the manufacture and separation of EpB which comprises the steps of:

I. feeding a gas comprising about 4 to 50 mole percent butadiene, about 5 to 30 mole percent oxygen and about 25 to 85 mole percent of butane to an epoxidation zone wherein butadiene is epoxidized to EpB in the presence of a silver catalyst;

II. removing from the epoxidation zone a gaseous epoxidation effluent comprising about 0.5 to 6 mole percent EpB, about 4 to 50 mole percent butadiene, about 4 to 25 mole percent oxygen and about 25 to 85 mole percent butane;

III. feeding the gaseous epoxidation effluent to a cooling/compression zone wherein the effluent is pressurized to a pressure of about 3 to 10 bars and cooled to a temperature of about 0° to 100° C.;

IV. feeding the effluent obtained from Step (III) to an absorption vessel wherein the effluent is intimately contacted with a mixture of liquid butane and butadiene at a pressure of about 3 to 6 bars and a temperature of about 10° to 50° C. to obtain:

(1) a vapor effluent comprising oxygen, about 25 to 85 mole percent butane, and about 4 to 50 mole percent butadiene from the upper section of the absorption vessel; and (2) a liquid effluent comprising EpB, butane and butadiene from the lower section of the absorption vessel;

V. recovering the effluent of Step IV (1) to the epoxidation zone; wherein the butadiene fed in Step I is provided by the effluent of Step IV (1), EpB is 3,4-epoxy-1-butene, butadiene is 1,3-butadiene, and butane is a saturated aliphatic or alicyclic hydrocarbon which contains 4 carbons.

9. Process according to claim 8 wherein the gas of Step I contains less than about 1 mole percent carbon dioxide.

10. Process according to claim 8 wherein the vapor effluent of Step IV (1) is fed to a carbon dioxide removal zone to obtain a carbon dioxide-depleted vapor effluent containing less than about 2 mole percent carbon dioxide and the carbon dioxide-depleted effluent is fed to the epoxidation zone.

11. Process according to claim 10 wherein the carbon dioxide removal zone comprises an absorption vessel wherein the vapor effluent of Step IV (1) is contacted with an aqueous solution of an alkali metal hydroxide or alkali metal carbonate.

12. Process for the manufacture and separation of EpB which comprises the steps of:

I. feeding a gas comprising about 4 to 50 mole percent butadiene, about 5 to 30 mole percent oxygen and about 25 to 85 mole percent butane to an epoxidation zone wherein butadiene is epoxidized to EpB in the presence of a silver catalyst;

II. removing from the epoxidation zone a gaseous epoxidation effluent comprising about 0.5 to 6 mole percent EpB, about 4 to 50 mole percent butadiene, about 4 to 25 mole percent oxygen and about 25 to 85 mole percent butane;

III. feeding the gaseous epoxidation effluent to a cooling/compression zone wherein the effluent is pressurized to a pressure of about 3 to 10 bars and cooled to a temperature of about 0° to 100° C.;

IV. feeding the effluent obtained from Step (III) to an absorption vessel wherein the effluent is intimately contacted with a mixture of liquid butane and butadiene at a pressure of about 3 to 6 bars and a temperature of about 10° to 50° C. to obtain:

(1) a vapor effluent comprising oxygen, about 40 to 80 mole percent butane and about 7 to 20 mole percent butadiene from the upper section of the absorption vessel; and (2) a liquid effluent comprising a solution containing about 2 to 40 weight percent EpB in a mixture of butane and butadiene from the lower section of the absorption vessel; and V. feeding the effluent of Step IV (1) to a carbon dioxide removal zone comprising an absorption vessel wherein the vapor effluent of Step IV (1) is contacted with an aqueous solution of an alkali metal hydroxide or alkali metal carbonate to obtain a carbon dioxide-depleted vapor effluent containing less than about 1 percent and feeding the carbon dioxide-depleted effluent to the epoxidation zone, wherein the butadiene and butane fed in Step I is provided by the carbon dioxide depleted effluent of Step V, EpB is 3,4-epoxy-1-butene and butadiene is 1,3-butadiene.

* * * * *